(12) United States Patent
Straub

(10) Patent No.: US 8,124,786 B2
(45) Date of Patent: Feb. 28, 2012

(54) MENTAL-CATALYZED PROCESS FOR PREPARATION OF SUBSTITUTED PYRAZOLECARBOXAMIDES

(75) Inventor: Alexander Straub, Wuppertal (DE)

(73) Assignee: Bayer CropScience AG, Monheim (DE)

( * ) Notice: Subject to any disclaimer, the term of this patent is extended or adjusted under 35 U.S.C. 154(b) by 112 days.

(21) Appl. No.: 12/373,218

(22) PCT Filed: Jul. 12, 2007

(86) PCT No.: PCT/EP2007/006177
§ 371 (c)(1),
(2), (4) Date: Sep. 28, 2009

(87) PCT Pub. No.: WO2008/006575
PCT Pub. Date: Jan. 17, 2008

(65) Prior Publication Data
US 2010/0056786 A1    Mar. 4, 2010

(30) Foreign Application Priority Data
Jul. 14, 2006    (DE) .......................... 10 2006 033 090

(51) Int. Cl.
*C07D 231/00* (2006.01)
(52) U.S. Cl. .................................................... 548/374.1
(58) Field of Classification Search ................ 548/374.1
See application file for complete search history.

(56) References Cited

U.S. PATENT DOCUMENTS

| 2004/0204470 | A1* | 10/2004 | Elbe et al. ................. 514/406 |
| 2007/0066673 | A1 | 3/2007 | Dunkel et al. |
| 2007/0196406 | A1 | 8/2007 | Dunkel et al. |

FOREIGN PATENT DOCUMENTS

| EP | 0824099 A1 | 2/1998 |
| WO | 03010149 A1 | 2/2003 |
| WO | 03074491 A1 | 9/2003 |
| WO | 2004103975 A1 | 12/2004 |
| WO | 2005042492 A1 | 5/2005 |
| WO | 2006061226 A1 | 6/2006 |
| WO | WO 2007/057140 | * 5/2007 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Kang, et al., "Copper-catalyzed N-Arylation of Aryl Iodides with Benzamides or Nitrogen Heterocycles in the Presence of Ethylenediamine", Synlett 3: 427-430 (2002), Georg Thieme Verlag, Stuttgart, Germany.
Klapars, et al., "A General and Efficient Copper Catalyst for the Amidation of Aryl Halides and the N-Arylation of Nitrogen Heterocycles", J. Am. Chem. Soc. 123: 7727-7729 (2001), American Chemical Society, Washington, DC 20036.
Klapars, et al., "A General and Efficient Copper Catalyst for the Amidation of Aryl Halides", J. Am. Chem. Soc. 124: 7421-7428 (2002), American Chemical Society, Washington, DC 20036.
Wolfe, et al., "Nickel-Catalyzed Amination of Aryl Chlorides", J. Am. Chem. Soc. 119: 6054-6058(1997), American Chemical Society, Washington, DC 20036.
Yang, et al., "Palladium-catalyzed amination of aryl halides and sulfonates", Journal of Organometallic Chemistry 576: 125-146 (1999), Elsevier Science, Lausanne, Switzerland.
Yin, et al., "Palladium-Catalyzed Intermolecular Coupling of Aryl Halides and Amides", Organic Letters 2: 1101-1104 (2000), American Chemical Society, Washington, DC 20036.
International Search Report for International (PCT) Application No. PCT/EP2007/006177, mailing date Jan. 2, 2008, WIPO, Geneva, Switzerland.

* cited by examiner

*Primary Examiner* — James O Wilson
*Assistant Examiner* — Douglas M Willis
(74) *Attorney, Agent, or Firm* — Sterne, Kessler, Goldstein & Fox P.L.L.C.

(57) ABSTRACT

The present invention provides a metal-catalyzed process for preparation of substituted pyrazolecarboxamides of formula (I) as fungicidally active compounds from 2-alkylhaloaromatics and heterocyclylamides.

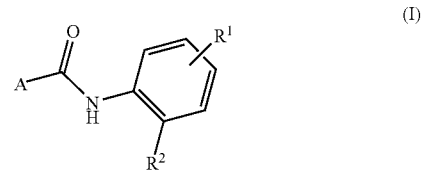

(I)

7 Claims, No Drawings

MENTAL-CATALYZED PROCESS FOR PREPARATION OF SUBSTITUTED PYRAZOLECARBOXAMIDES

CROSS REFERENCE TO RELATED APPLICATIONS

Not applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

The present invention relates to a process for preparing known fungicidally active alkylanilides from 2-alkylhaloaromatics and heterocyclylamides.

EP-A-0 824 099 and WO-A-03010149 disclose that alkylanilides are obtained by reacting the appropriate acid chloride with the appropriate alkylaniline derivative.

Both preparation and handling of the acid chlorides and the preparation of the alkylanilides are associated with a considerable level of technical complexity. For example, the acid chlorides have to be purified before the reaction by a time-consuming and costly distillation step.

The anilines are prepared typically, as described in WO-A-3074491, by a complicated synthesis from the corresponding bromoaromatics and benzophenone imine or at temperatures of 150° C. and pressures of from 75 to 85 bar with ammonia gas, as described in WO-A-06061226.

Alkylanilines, however, frequently exhibit toxic properties and are potentially mutagenic.

The prior art discloses that aryl halides can be reacted with amides under palladium or copper catalysis to give alkylanilides (J. Am. Chem. Soc. 2002, 124, 7420).

It is frequently found, however, that metal-catalyzed reactions with heterocycles which can function as chelating ligands are inhibited. Furthermore, ortho-substituted haloaromatics are sterically hindered for a halogen exchange.

BRIEF SUMMARY OF THE INVENTION

It is therefore an object of the present invention to provide a process for simple and selective preparation of alkylanilides, which does not have the disadvantages described in the prior art.

Surprisingly, conditions have been found under which heterocyclylamides can be reacted efficiently with ortho-substituted haloaromatics.

The present invention thus provides a process for preparing alkylanilides of the formula (I)

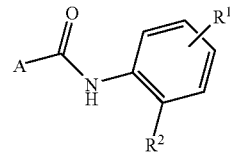

in which
$R^1$ is hydrogen, halogen, —CR' (R'=hydrogen, fluorine or O—$C_{1-4}$-alkyl), more preferably hydrogen;
$R^2$ is —CH(Me)—$CH_2$—$CHMe_2$, —$CH_2$—$CH_2$-t-But, or

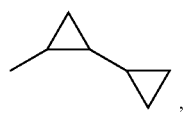

particular preference being given to —CH(Me)—$CH_2$—$CHMe_2$ and

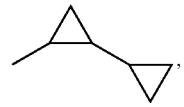

A is the radical of the formula (A1)

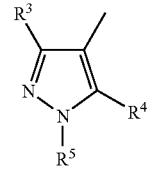

in which
$R^3$ is hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case from 1 to 5 halogen atoms, aminocarbonyl or aminocarbonyl-$C_1$-$C_4$-alkyl;
$R^4$ is hydrogen, halogen, cyano, $C_1$-$C_4$-alkyl, $C_1$-$C_4$-alkoxy or $C_1$-$C_4$-alkylthio;
$R^5$ is hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case from 1 to 5 halogen atoms, or phenyl;
or
A is the radical of the formula (A2)

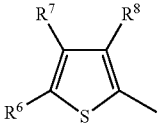

in which
$R^6$ and $R^7$ are each independently hydrogen, halogen, $C_1$-$C_4$-alkyl or $C_1$-$C_4$-haloalkyl having from 1 to 5 halogen atoms,
$R^8$ is halogen, cyano or $C_1$-$C_4$-alkyl, or $C_1$-$C_4$-haloalkyl or $C_1$-$C_4$-haloalkoxy having in each case from 1 to 5 halogen atoms,
or
A is the radical of the formula (A3)

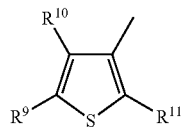

(A3)

in which
$R^9$ and $R^{10}$ are each independently hydrogen, halogen, $C_1$-$C_4$-alkyl or $C_1$-$C_4$-haloalkyl having from 1 to 5 halogen atoms,
$R^{11}$ is hydrogen, halogen, $C_1$-$C_4$-alkyl or $C_1$-$C_4$-haloalkyl having from 1 to 5 halogen atoms,
or
A is the radical of the formula (A4)

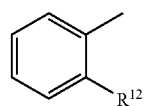

(A4)

in which
$R^{12}$ is hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case from 1 to 5 halogen atoms,
or
A is the radical of the formula (A5)

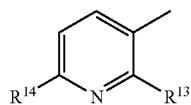

(A5)

in which
$R^{13}$ is halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case from 1 to 5 halogen atoms,
$R^{14}$ is hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case from 1 to 5 halogen atoms, $C_1$-$C_4$-alkylsulfinyl or $C_1$-$C_4$-alkylsulfonyl,
or
A is the radical of the formula (A6)

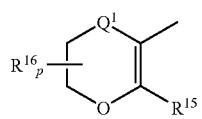

(A6)

in which
$R^{15}$ is $C_1$-$C_4$-alkyl or $C_1$-$C_4$-haloalkyl having from 1 to 5 halogen atoms,
$R^{16}$ is $C_1$-$C_4$-alkyl,
$Q^1$ is S (sulfur), O (oxygen), SO, $SO_2$ or $CH_2$,
p is 0, 1 or 2, where $R^{16}$ represents identical or different radicals when p is 2,
or
A is the radical of the formula (A7)

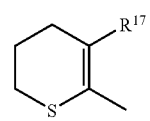

(A7)

in which
$R^{17}$ is $C_1$-$C_4$-alkyl or $C_1$-$C_4$-haloalkyl having from 1 to 5 halogen atoms,
or
A is the radical of the formula (A8)

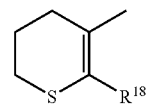

(A8)

in which
$R^{18}$ is $C_1$-$C_4$-alkyl or $C_1$-$C_4$-haloalkyl having from 1 to 5 halogen atoms,
or
A is the radical of the formula (A9)

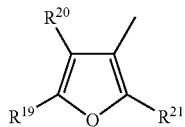

(A9)

in which
$R^{19}$ and $R^{20}$ are each independently hydrogen, halogen, amino, $C_1$-$C_4$-alkyl or $C_1$-$C_4$-haloalkyl having from 1 to 5 halogen atoms,
$R^{21}$ is hydrogen, halogen, $C_1$-$C_4$-alkyl or $C_1$-$C_4$-haloalkyl having from 1 to 5 halogen atoms,
or
A is the radical of the formula (A10)

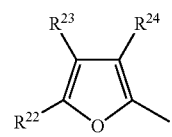

(A10)

in which
$R^{22}$ and $R^{23}$ are each independently hydrogen, halogen, amino, nitro, $C_1$-$C_4$-alkyl or $C_1$-$C_4$-haloalkyl having 1 to 5 halogen atoms,
$R^{24}$ is hydrogen, halogen, $C_1$-$C_4$-alkyl or $C_1$-$C_4$-haloalkyl having from 1 to 5 halogen atoms, or A is the radical of the formula (A11)

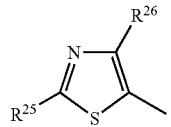
(A11)

in which $R^{25}$ is hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having from 1 to 5 halogen atoms, $R^{26}$ is halogen, $C_1$-$C_4$-alkyl or $C_1$-$C_4$-haloalkyl having from 1 to 5 halogen atoms, or A is the radical of the formula (A12)

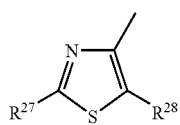
(A12)

in which $R^{27}$ is hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having from 1 to 5 halogen atoms, $R^{28}$ is halogen, $C_1$-$C_4$-alkyl or $C_1$-$C_4$-haloalkyl having from 1 to 5 halogen atoms, or A is the radical of the formula (A13)

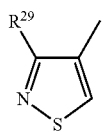
(A13)

in which $R^{29}$ is halogen, $C_1$-$C_4$-alkyl or $C_1$-$C_4$-haloalkyl having from 1 to 5 halogen atoms, or A is the radical of the formula (A14)

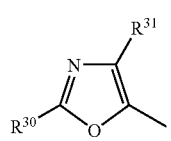
(A14)

in which $R^{30}$ is hydrogen or $C_1$-$C_4$-alkyl, $R^{31}$ is halogen or $C_1$-$C_4$-alkyl, or A is the radical of the formula (A15)

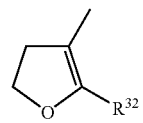
(A15)

in which $R^{32}$ is $C_1$-$C_4$-alkyl or $C_1$-$C_4$-haloalkyl having from 1 to 5 halogen atoms, or A is the radical of the formula (A16)

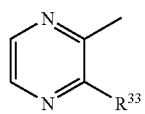
(A16)

in which $R^{33}$ is hydrogen, halogen, $C_1$-$C_4$-alkyl or $C_1$-$C_4$-haloalkyl having from 1 to 5 halogen atoms, or A is the radical of the formula (A17)

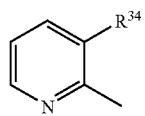
(A17)

in which $R^{34}$ is halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case from 1 to 5 halogen atoms, or A is the radical of the formula (A18)

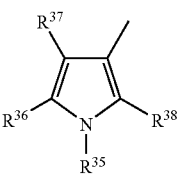
(A18)

in which $R^{35}$ is hydrogen, cyano, $C_1$-$C_4$-alkyl, $C_1$-$C_4$-haloalkyl having from 1 to 5 halogen atoms, $C_1$-$C_4$-alkoxy-$C_1$-$C_4$-alkyl, hydroxy-$C_1$-$C_4$-alkyl, $C_1$-$C_4$-alkylsulfonyl, di($C_1$-$C_4$-alkyl)aminosulfonyl, $C_1$-$C_6$-alkylcarbonyl or in each case optionally substituted phenylsulfonyl or benzoyl, $R^{36}$ is hydrogen, halogen, $C_1$-$C_4$-alkyl or $C_1$-$C_4$-haloalkyl having from 1 to 5 halogen atoms, $R^{37}$ is hydrogen, halogen, cyano, $C_1$-$C_4$-alkyl or $C_1$-$C_4$-haloalkyl having from 1 to 5 halogen atoms, $R^{38}$ is hydrogen, halogen, $C_1$-$C_4$-alkyl or $C_1$-$C_4$-haloalkyl having from 1 to 5 halogen atoms, or
A is the radical of the formula (A19)

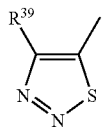
(A19)

in which
$R^{39}$ is $C_1$-$C_4$-alkyl,
characterized in that,
in a first step, carboxamides of the formula (II)

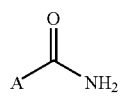
(II)

in which the A radical is as defined above
are reacted with haloalkylbenzenes of the formula (III)

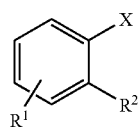
(III)

in which
the $R^1$ and $R^2$ radicals are each as defined above and the substituent $R^1$ is preferably in the meta or para position, more preferably in the 4 position (para to X) of the aromatic; and
the X radical is a halogen, preferably Cl or Br, more preferably Br,
in a metal-catalyzed reaction.

The present invention further relates to compounds of the formula (III)

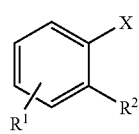
(III)

where
$R^1$ is hydrogen, halogen, –CR'(CF$_3$)$_2$ (R'=hydrogen, fluorine or O—$C_{1-4}$-alkyl), more preferably hydrogen, and the substituent $R^1$ is preferably in the meta or para position, more preferably in the 4 position (para to X) of the aromatic; and
$R^2$ is —CH(Me)—CH$_2$—CHMe$_2$ and —CH$_2$—CH$_2$-t-But,
or
$R^1$ is halogen, —CR'(CF$_3$)$_2$ (R'=hydrogen, fluorine or O-$C_{1-4}$-alkyl), more preferably hydrogen, and the substituent $R^1$ is preferably in the meta or para position, more preferably in the 4 position (para to X) of the aromatic; and $R^2$ is

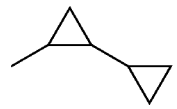

and
X is a halogen, preferably Cl or Br, more preferably Br.

The present invention additionally relates to the compounds of the formulae (IV) to (VI)

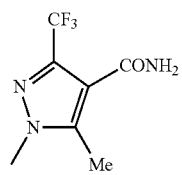
(IV)

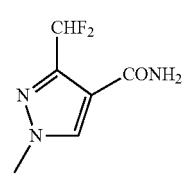
(V)

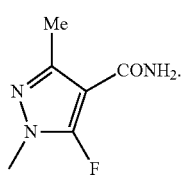
(VI)

A further aspect of the present invention relates to the use of the compounds of one of the formulae (II), (III), (IV), (V) and (VI) as reactants/intermediates in the process according to the invention described above.

BRIEF DESCRIPTION OF THE SEVERAL VIEWS OF THE DRAWINGS

Not applicable.

DETAILED DESCRIPTION OF THE INVENTION

The inventive reaction will be described in detail with reference to scheme (I) below:

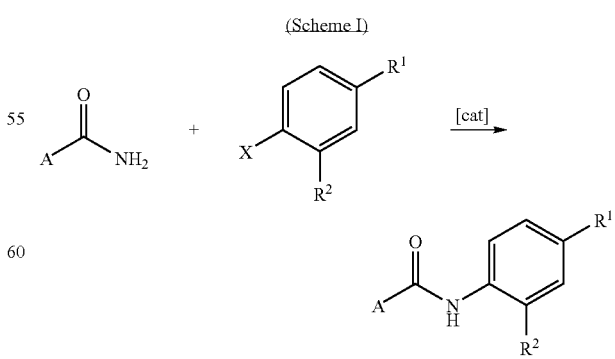
(Scheme I)

In connection with the present invention, the term "halogen" (X) encompasses elements which are selected from the group consisting of fluorine, chlorine, bromine and iodine, preference being given to using chlorine and bromine, and particular preference to using bromine.

Optionally substituted radicals may be mono- or polysubstituted, where the substituents may be the same or different in the case of polysubstitutions.

The definition "$C_1$-$C_6$-alkyl" encompasses the largest range for an alkyl radical defined herein. Specifically, this definition encompasses the meanings of methyl, ethyl, n-, isopropyl, n-, iso-, sec-, tert-butyl, and in each case all isomeric pentyls and hexyls.

A further possibility is that of reacting 2-halobenzaldehydes with Wittig reagents, in which case the propenone derivatives thus obtained, as described in WO-A-03074491, can be converted to cyclopropyl compounds.

Other possibilities are the hydroxyalkylation of aromatics or metalated aromatics with ketones or acid chlorides and, respectively, the subsequent elimination and reduction thereof. Proceeding from 1,2-dibromobenzene, this is illustrated by way of example in scheme (II):

(Scheme II)

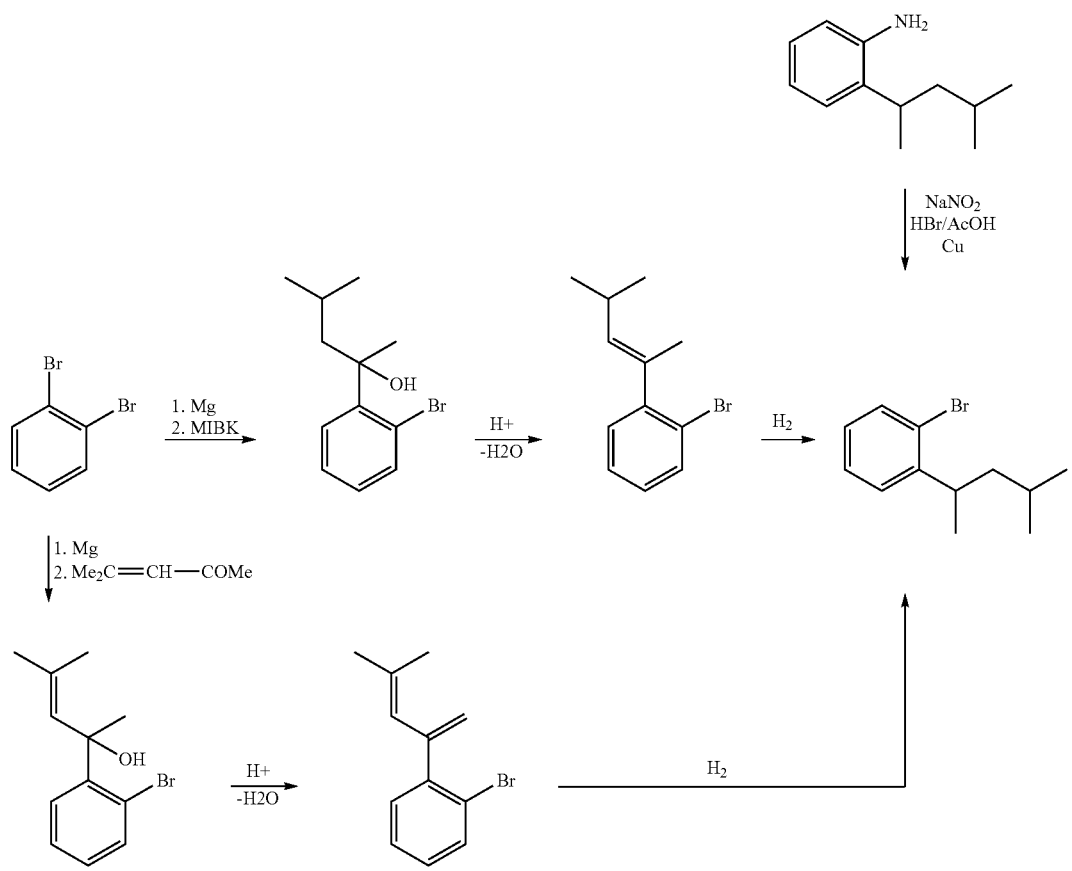

The definition "$C_2$-$C_6$-alkenyl" encompasses the largest range for an alkenyl radical defined herein. Specifically, this definition encompasses the meanings of ethenyl, n-, isopropenyl, n-, iso-, sec-, tert-butenyl, and in each case all isomeric pentenyls and hexenyls.

The inventive compounds can optionally be used as mixtures of different possible isomeric forms, especially of stereoisomers, for example E and Z, threo and erythro, and also optical isomers, and if appropriate also of tautomers. It is possible to use both the E and the Z isomers, and also the threo and erythro isomers, and also the optical isomers, any mixtures of these isomers, and also the possible tautomeric forms.

The haloalkylbenzenes required are known in the prior art, for example from WO-A-03074491, or can be prepared by known methods by Friedel-Crafts alkylation or electrophilic aromatic halogenation.

Alternatively, it is also possible to obtain the halogen compounds in question from aniline derivatives by diazotization and Sandmeyer reaction.

According to the present invention, the haloalkylbenzene of the formula (IX)

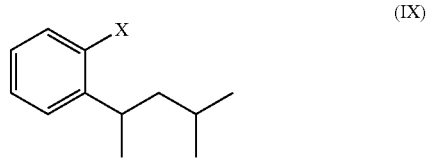

(IX)

in which X is a halogen atom, especially Br, is a preferred reactant.

Only some of the acid amides required are known, and they can be obtained from known acid halides, acids, esters or nitrites by known reactions.

This will be illustrated by the following example according to scheme (III):

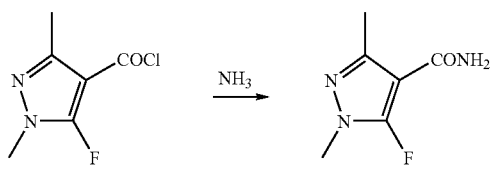

(Scheme III)

The nitrogen source used may be aqueous or gaseous ammonia or one of its salts, for example ammonium acetate or sodium amide.

Useful solvents for the preparation of the acid amides include all solvents which are stable under the reaction conditions, for example ethers such as THF, 2-methyl-THF, dioxane, methyl t-butyl ether (MTBE), diethylene glycol, diethoxymethane, dimethoxymethane; aromatic hydrocarbons such as toluene, xylene, chlorobenzene, dichlorobenzene, benzene; aliphatic hydrocarbons such as petroleum ether, heptane, hexane, methylcyclohexane, cyclohexane; dimethylformamide (DMF); dimethylacetamide; N-methylpyrrolidone (NMP); dimethyl sulfoxide (DMSO), acetonitrile; butyronitrile; water; ketones such as acetone, methyl isobutyl ketone (MIBK); alcohols such as methanol, ethanol, isopropanol.

For the inventive reaction of the acid amide with the halobenzene derivative, metal catalysts are used. For this purpose, palladium and copper in all oxidation states are useful, for example in metallic form or in the form of salts.

According to the present invention, for example, $Pd(OAc)_2$, $Pd(OH)_2$, $PdCl_2$, $Pd(acac)_2$ (acac=acetylacetonate), $Pd(NO_3)_2$, $Pd(dba)_2$, $Pd_2dba_3$, (dba=dibenzylideneacetone), dichlorobis(triphenylphosphine)palladium(II), $Pd(CH_3CN)_2Cl_2$, tetrakis(triphenylphosphine)palladium(0), Pd/C or palladium nanoparticles, CuI, CuCl, CuSCN, $Cu_2O$, CuO, $CuCl_2$, $CuSO_4$, CuBr, $CuBr_2$, $Cu_2S$, $Cu(OAc)_2$, $Cu(acac)_2$ are suitable, preference being given to using the copper compounds or mixtures thereof.

According to the present invention, the catalysts are used in catalytic amounts. This means that the metal catalysts are used in concentrations of from 0.01 to 50.0 mol %, preferably of 1.0 to 20.0 mol %, based on the carboxamides of the formula (II).

The inventive reaction is preferably performed in the presence of ligands.

In the case of palladium catalysis, suitable ligands are, for example, selected from the group of carbene and phosphine ligands, particular preference being given to using xantphos and tris(t-butyl)phosphine.

In the case of copper catalysis, suitable ligands are, for example, selected from the group consisting of diamines, for example N,N'-dimethyl-1,2-cyclohexanediamine (cis or trans, racemic or as an enantiomer), N,N'-dimethylethylenediamine, ethylenediamine, N-methylethylenediamine, N-butylethylenediamine, N,N,N'-trimethylethylenediamine or else 1,10-phenanthroline, ethylenediaminetetraacetic acid, tetra-n-butylammonium fluoride, tris(3,6-trioxaheptyl)amine (TDA-1), particular preference being given to using N,N'-dimethyl-1,2-cyclohexanediamine.

The ligands are added to the metal catalyst in such a ratio that the desired catalytic action occurs.

According to the present invention, the ratio of ligand to metal catalyst is between 0.5 to 10 equivalents, preferably between 1 to 5 equivalents.

The reaction is preferably carried out in the presence of bases. Useful examples include alkali metal and alkaline earth metal hydroxides such as KOH, NaOH, $Ca(OH)_2$, fluorides such as KF, phosphates such as $K_3PO_4$, and carbonates such as potash, soda, cesium carbonate or phosphazene bases, alkoxides such as sodium tert-butoxide, or phenoxides such as sodium phenoxide.

According to the present invention, the bases are used in concentrations of from 0.5 to 5 equivalents, preferably from 1.0 to 3 equivalents, based on the carboxamides of the formula (II).

The inventive reaction of the acid amide with the halobenzene derivative is preferably carried out in a solvent.

The solvents used are preferably dioxane, THF, diglyme, toluene, xylene, DMF.

According to the present invention, the acid amides and the halobenzene derivatives are reacted with one another in an equimolar ratio. In an alternative embodiment, the halobenzene derivative can also be used in excess, for example as a solvent.

According to the invention, the acid amides are reacted with the halobenzene derivatives at temperatures in the range from 20 to 200° C., preferably from 70 to 150° C.

In a particularly preferred embodiment of the invention, carboxamides of the formula (V) are reacted with compounds of the formula (X)

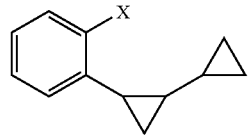

(X)

in which the X radical is a halogen
to give carboxamides of the formula (XI)

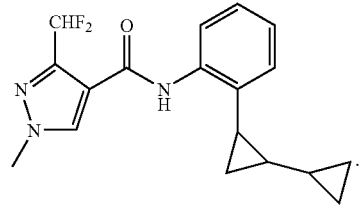

(XI)

The examples which follow are intended to illustrate the subject matter of the invention in detail, but without restricting it thereto.

EXAMPLE 1

1-Bromo-2-(1,3-dimethylbutyl)benzene 28.4 g of 2-(1,3-dimethylbutyl)aniline in 134.9 g (667 mmol) of 40 percent hydrobromic acid in glacial acetic acid at 10° C. are admixed with 12.5 g (181 mmol) of sodium nitrite in portions with stirring within 1.5 h. Thereafter, 0.5 g of copper powder is added and the mixture is boiled under reflux for 1 h hour. Subsequently, 120 ml of water and sodium hydroxide solution are added until pH 12 is attained, and the organic phase is removed, washed with dilute hydrochloric acid and concentrated by evaporation under reduced pressure. After distillation in a Kugelrohr apparatus at 0.3 mbar/70° C. and purification of the main fraction by means of preparative HPLC, 8.3 g of a yellowish oil with a purity of 99.4% (determined by HPLC) are obtained.

$^1$H NMR (400 MHz, CDCl$_3$): 0.89 (dd, 6H), 1.17 (d, 3H), 1.32-1.38 and 1.46-1.53 (2m, AB, 2×1H), 1.54-1.6 (m, 1H), 3.34 (m, 1H), 7 (m, 1H), 7.21-7.28 (m, 2H), 7.52 (d, 1H).

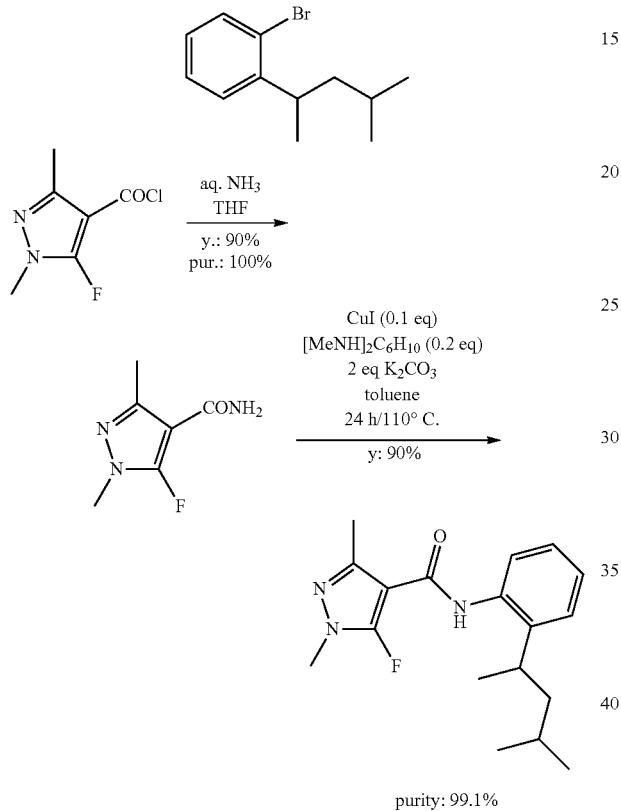

5-Fluoro-1,3-dimethyl-1 H-pyrazole-4-carboxamide 19.9 g of 5-fluoro-1,3-dimethyl-1H-pyrazole-4-carbonyl chloride are added dropwise at 20-35° C. to a mixture of 35 g of 25 percent aqueous ammonia and 170 ml of THF. After stirring for 4 h, the organic solvent fraction is concentrated by evaporation under reduced pressure and 0.2 mol of potash and sodium chloride are added to saturation. After extracting four times with ethyl acetate and concentrating the combined organic phases by evaporation under reduced pressure, 16.6 g of a yellow solid are obtained.

$^1$H NMR (400 MHz, d$^6$-DMSO): 2.64 (s, 3H), 3.63 (s, 3H), 6.9 (broad s, 1H), 7.18 (broad s, 1H).

N-[2-(1,3-Dimethylbutyl)phenyl]-5-fluoro-1,3-dimethyl-1H-pyrazole-4-carboxamide

A mixture of 0.221 g (1.16 mmol) of copper iodide, 3.21 g (23.22 mmol) of potash and 2.189 g of 5-fluoro-1,3-dimethyl-1H-pyrazole-4-carboxamide is admixed under argon with 330 mg (2.322 mmol) of N,N'-dimethyl-1,2-cyclohexanediamine, 2.8 g (11.6 mmol) of 1-bromo-2-(1,3-dimethylbutyl)benzene and 30 ml of toluene. After boiling under reflux for one day, the mixture is poured onto water and 10 ml of a 5% EDTA solution. Subsequently, the mixture is extracted three times with ethyl acetate and concentrated by evaporation under reduced pressure. The oily residue is dissolved in toluene and stirred into n-hexane. After the precipitated crystals have been filtered off with suction, 3.3 g (89% of the theoretical yield) of N-[2-(1,3-dimethylbutyl)phenyl]-5-fluoro-1,3-dimethyl-1H-pyrazole-4-carboxamide are obtained with a purity (HPLC) of 99%.

The invention claimed is:

1. A process for preparing carboxamides of the formula (I)

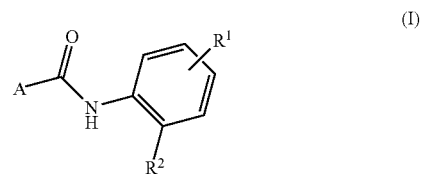

in which

R$^1$ is hydrogen, halogen, —C(R')$_3$ where R' is hydrogen, fluorine or O—C$_{1-4}$-alkyl;

R$^2$ is —CH(Me)—CH$_2$—CH(Me)$_2$, —CH$_2$—CH$_2$-t-But, or

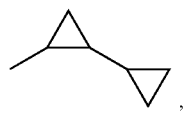

A is formula (A1)

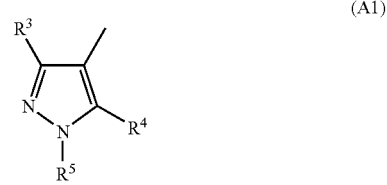

in which

R$^3$ is hydrogen, cyano, halogen, nitro, C$_1$-C$_4$-alkyl, C$_1$-C$_4$-alkoxy, C$_1$-C$_4$-alkylthio, C$_3$-C$_6$-cycloalkyl, C$_1$-C$_4$-haloalkyl, C$_1$-C$_4$-haloalkoxy, aminocarbonyl, aminocarbonyl-C$_1$-C$_4$-alkyl, or C$_1$-C$_4$ haloalkylthio having from 1 to 5 halogen atoms;

R$^4$ is halogen;

R$^5$ is hydrogen, C$_1$-C$_4$-alkyl, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkoxy-C$_1$-C$_4$-alkyl, C$_1$-C$_4$-haloalkyl, C$_1$-C$_4$-haloalkylthio-C$_1$-C$_4$-alkyl wherein C$_1$-C$_4$-haloalkoxy-C$_1$-C$_4$-alkyl has, in each case, from 1 to 5 halogen atoms, or phenyl;

comprising reacting a carboxamide of the formula (II)

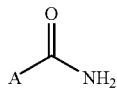
(II)

with a haloalkylbenzene of the formula (III)

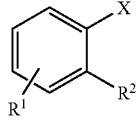
(III)

in which X is halogen
in a metal-catalyzed reaction wherein metal catalyst is selected from the group consisting of palladium and copper catalysts.

2. The process as claimed in claim 1, wherein the carboxamide of formula (VI)

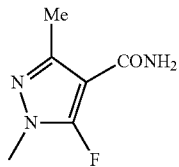
(VI)

is converted to a carboxamide of the formula (VIII)

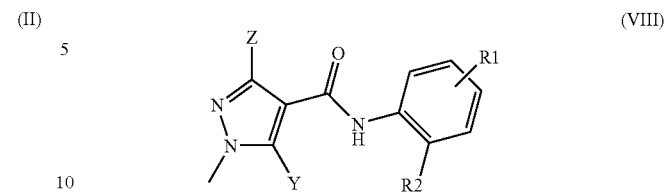
(VIII)

wherein
Z is methyl, and
Y is fluorine.

3. The process as claimed in any one of claims 1 and 2, characterized in that at least one copper catalyst is used in the presence of a ligand, wherein said ligand is selected from the group consisting of N,N'-dimethyl-1,2-cyclohexanediamine, N,N'-dimethylethylenediamine, ethylenediamine, N-methylethylenediamine, N-butylethylenediamine, N,N,N'-trimethylethylenediamine, 1,10-phenanthroline, ethylenediaminetetraacetic acid, tetra-n-butylammonium fluoride, and tris(3,6-trioxaheptyl)amine (TDA-1).

4. The process as claimed in claim 3, wherein said ligand is a diamine.

5. The process as claimed in claim 3 using a base.

6. The process as claimed in claim 4 using a base.

7. The process as claimed in any one of claims 1 and 2 using a base.

* * * * *